US009610380B2

(12) United States Patent
DiMauro

(10) Patent No.: US 9,610,380 B2
(45) Date of Patent: Apr. 4, 2017

(54) VERTEBRAL BODY AUGMENTATION SYSTEMS COMPRISING MICROBUBBLES

(71) Applicant: DePuy Synthes Products, Inc., Raynham, MA (US)

(72) Inventor: Thomas M DiMauro, Southboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 391 days.

(21) Appl. No.: 14/316,135

(22) Filed: Jun. 26, 2014

(65) Prior Publication Data

US 2015/0374879 A1 Dec. 31, 2015

(51) Int. Cl.
*A61F 2/46* (2006.01)
*A61L 24/06* (2006.01)
*A61L 24/00* (2006.01)
*A61M 25/10* (2013.01)
*A61L 29/14* (2006.01)

(52) U.S. Cl.
CPC .............. *A61L 24/06* (2013.01); *A61L 24/001* (2013.01); *A61L 29/14* (2013.01); *A61M 25/1006* (2013.01); *A61L 2400/06* (2013.01); *A61L 2430/02* (2013.01); *A61L 2430/38* (2013.01); *A61M 2210/02* (2013.01)

(58) Field of Classification Search
CPC combination set(s) only.
See application file for complete search history.

(56) References Cited

U.S. PATENT DOCUMENTS

| 4,751,921 A * | 6/1988 | Park ................... A61B 17/8827 604/190 |
| 8,360,629 B2 | 1/2013 | Globerman |
| 2010/0178250 A1 | 7/2010 | Forbes |
| 2013/0211249 A1 | 8/2013 | Barnett |

OTHER PUBLICATIONS

Moran, In Vitro Acoustic Characterisation of Four Intravenous Ultrasonic Contrast Agents at 30 MHz, *Ultrasound in Medicine and Biology*, vol. 28, No. 6, 2002, pp. 785-791.
Gi, Contrast-Enhanced Ultrasound with Perflubutane Microbubbles for Femoral Nerve Block—A Human Cadaver Study, A3274, Oct. 14, 2013, American Society of Anesthesiologists.
Schneider, Characteristics of SonoVue, *Echocardiography*, Oct. 1999;16(7, Pt 2):743-746,.
Kratzer, Contrast-enhanced wideband harmonic imaging ultrasound (SonoVue): a new technique for quantifying bowel wall vascularity in Crohn's disease, *Scand J Gastroenterol.* Aug. 2005;40(8):985-91)—abstract.

* cited by examiner

*Primary Examiner* — Sameh Boles

(57) ABSTRACT

Adding gas-filled microbubbles to both the saline solution of either a kyphoplasty balloon or a vertebroplasty cement allows the clinician to assess via ultrasound both the location and expansion of the balloon and the location of the cement during vertebral body augmentation procedures without the use of fluoroscopy.

6 Claims, 1 Drawing Sheet

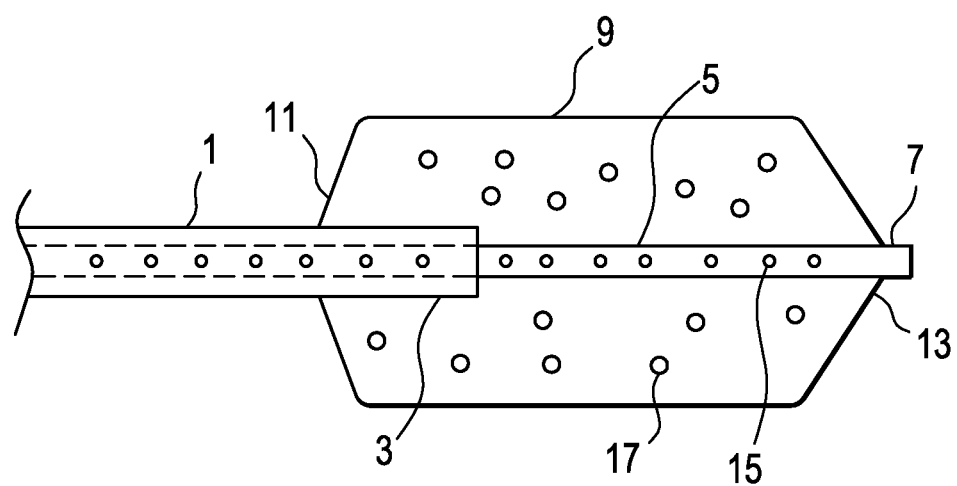

US 9,610,380 B2

VERTEBRAL BODY AUGMENTATION SYSTEMS COMPRISING MICROBUBBLES

BACKGROUND OF THE INVENTION

In vertebroplasty, the clinician or surgeon seeks to treat a compression fracture of a vertebra by injecting a curable bone cement such as polymethylmethacrylate (PMMA) into the fracture. In a related procedure called kyphoplasty, the clinician or surgeon first inflates a balloon in the vertebra to create cavity, and then injects the curable bone cement into the cavity. Each procedure is considered to be a form of vertebral body augmentation (VBA).

In current vertebral body augmentation techniques, there are two instances in which fluoroscopy is used: balloon placement and cement injection.

When using a balloon to create a cavity in the vertebral body, the clinician first places the balloon in the vertebral body, expands it using saline, assesses the location and expansion of the balloon via fluoroscopy, adjusts the location and/or expansion of the balloon if needed, and then deflates and removes the balloon.

When performing cement injection, the clinician uses fluoroscopy for needle placement and for monitoring the injection of bone cement within the vertebral body. Using a simple syringe, the clinician is exposed to excessive x-ray radiation within a fluoro field produced by a fluoroscope.

It is well known that excessive exposure to x-ray radiation is dangerous and even cancer-causing.

Therefore, it is an object of the present invention to eliminate the use of fluoroscopy from VBA procedures.

SUMMARY OF THE INVENTION

It is noted that FDA-approved microbubbles (such as those in Sonovue™) are seen very clearly under ultrasound, and so could provide a means of assessing the location of both balloon and cement during VBA procedures.

It is believed that adding FDA-approved microbubbles to both the saline solution of the balloon and the cement could allow the VBA clinician to assess both the location and expansion of the balloon and the location of the cement during VBA procedures.without the use of fluoroscopy.

Therefore, in accordance with the present invention, there is provided a bone cement formulation comprising:
 a) a powder component comprising: i) an acrylic polymer powder, and ii) an initiator powder present in an amount defining a powder initiator fraction,
 b) a liquid component comprising i) an acrylic monomer and ii) an accelerator present in an amount defining a liquid accelerator fraction,
 c) a solution comprising a plurality of microbubbles.

Also in accordance with the present invention, there is provided a cured bone cement comprising a plurality of microbubbles.

Also in accordance with the present invention, there is provided a system comprising:
 a) an inflated balloon having an opening;
 b) a tube connected to the opening;
 c) a fluid disposed within the inflated balloon; and
 d) a plurality of microbubbles dispersed within the fluid.

Also in accordance with the present invention, there is provided a tool comprising an outer tube having a distal end, an catheter tube extending within the outer tube and having a distal end region that extends beyond the distal end of the outer tube, and an expandable structure having a proximal end secured to the distal end of the outer tube and a distal end secured to the distal end region of the inner tube, whereby the distal end region of the inner tube is enclosed within the expandable structure, wherein the inner tube is filled with a fluid, wherein a plurality of microbubbles are disposed within the fluid of the inner tube.

Also in accordance with the present invention, there is provided a tool comprising an outer tube having a distal end, an catheter tube extending within the outer tube and having a distal end region that extends beyond the distal end of the outer tube, and an expandable structure having a proximal end secured to the distal end of the outer tube and a distal end secured to the distal end region of the inner tube, whereby the distal end region of the inner tube is enclosed within the expandable structure, wherein the expandable structure is filled with a fluid, wherein a plurality of microbubbles are disposed within the fluid of the expandable structure.

Also in accordance with the present invention, there is provided a method for treating bone comprising the steps of:
 a) providing a tool comprising an outer tube having a distal end, an inner tube extending within the outer catheter tube and having a distal end region that extends beyond the distal end of the outer tube, and an expandable structure having a proximal end secured to the distal end of the outer tube and a distal end secured to the distal end region of the inner tube, whereby the distal end region of the inner tube is enclosed within the expandable structure, wherein a first plurality of microbubbles are disposed with the inner tube in a first fluid and a second plurality of microbubbles are disposed within the expandable structure in a second fluid,
 b) manipulating the tool to introduce the expandable structure into bone while in a generally collapsed geometry,
 c) applying ultrasound to assess a location of the inner catheter,
 d) causing the expandable structure to assume an expanded geometry inside bone, and
 e) applying ultrasound to assess a location of the expandable structure.

DESCRIPTION OF THE FIGURES

FIG. 1 discloses a dual lumen catheter of the present invention having a first plurality of microbubbles disposed within a first fluid in the inner tube and a second plurality of microbubbles disposed within a second fluid within the expandable structure.

DETAILED DESCRIPTION OF THE INVENTION

In one preferred embodiment, the powder component of the cement of the present invention comprises:
 a) about 60-90 wt % PMMA having a molecular weight of less than 500,000 (preferably between 150,000 and 300,000; more preferably between 270,000 and 300,000);
 b) about 1 wt % PMMA having a molecular weight of between about 500,000 and 600,000, and containing the polymerization inhibitor;
 c) about 1-4 wt % PMMA (preferably 2-3 wt %) having a molecular weight of between about 600,000 to about 5,000,000 (preferably between about 1,000,000 and about 4,000,000; more preferably between 3,000,000 and 4,000,000);

d) about 5-35 wt % radiopaque agent (preferably, barium sulfate);
e) about 0.1-1 wt % initiator (preferably, benzoyl peroxide);

In another embodiment, the powder component of the cement of the present invention comprises:
a) about 15-30 wt % PMMA having a particle size of less than about 5 um (preferably having a median of about 3 um);
b) about 15-30 wt % PMMA having a particle size of between about 5 and 20 (preferably having a median of about 10 um), and containing the polymerization inhibitor;
c) about 35-65 wt % PMMA (preferably 40-50 wt %) having a particle size of at least about 20 um (preferably having a median of about 100 um);
f) about 5-35 wt % radiopaque agent (preferably, barium sulfate).
g) about 0.1-1 wt % initiator (preferably, benzoyl peroxide)

In one embodiment, the liquid component of the cement of the present invention comprises:
a) about 97-99 vol % methyl methacrylate;
b) about 1-3 vol % DmpT
c) about 10-50 ppm hydroquinone The initiator component of the powder helps start the free radical polymerization of the PMMA. It is typically present in the powder in an amount of 0.1-1 wt %. Typically, it is benzoyl peroxide.

The liquid acrylic monomer undergoes a free radical polymerization to form the PMMA cement. It is typically present in the liquid in an amount of 97-99 vol %. It is typically methylmethacrylate. (MMA).

The accelerator component of the liquid speeds the free radical polymerization of the PMMA. It is typically present in the liquid in an amount of 1-3 vol %. Typically, it is DmpT.

The microbubbles of the present invention are preferably smaller than one millimeter in diameter, but larger than one micron. The gas-filled, e.g. air or perfluorocarbon, microbubbles oscillate and vibrate when a sonic energy field is applied and may reflect ultrasound waves. This distinguishes the microbubbles from surrounding tissues. In practice, because gas bubbles in liquid lack stability and would therefore quickly dissolve, microbubbles must be encapsulated with a solid shell. The shell is made from either a lipid (such as a phospholipid (such as in Sonovue)) or a protein (such as those in Optison), whose microbubbles consist of perfluoropropane gas encapsulated by a serum albumin shell.

Suitable microbubbles are generally available. Some commercial products that contain such suitable microbubbles are believed to include:
a) Optison™, which comprises hollow albumin microbubbles filled with octafluoropropane;
b) Sonovue™, which comprises phospholipid microbubbles filled with sulfur hexafluoride;
c) Albunex™, which comprises hollow albumin microbubbles filled with air;
d) Sonozoid™, which comprises hydrogenated egg-yolk phosphatidyl serine sodium microbubbles in perfluorobutane;

Generally, these microbubbles are available in an aqueous (e.g. saline) solution. For use in the cement embodiment of the present invention, any suitable evaporation technology may be employed to obtain the dry microbubbles. For use in the balloon/tube embodiments, the commercial product may be suitably diluted to obtain preferred microbubble concentrations.

Preferably, the microbubble concentration in the powder/liquid mixture is in the range of 0.001 to 100 million microbubbles/ml of the liquid, preferably, in the range of 0.1 to 10 million microbubbles/ml of the liquid most preferably. in the range of 1 to 10 million microbubbles/ml of the liquid. Moran, *Ultrasound in Medicine and Biology,* 28, 6, 2002, 785-791, reports that most microbubble formulations exhibited a peak in mean backscatter power between 1 and 10 million microbubbles/mL. The Sonovue microbubble had a peak at 100 million microbubbles/mL, the highest concentration tested.

In one embodiment, the microbubbles comprise those in Sonazoid®, a second-generation ultrasound contrast agent that is composed of perfluorobutane encapsulated in hydrogenated egg-yolk phosphatidyl serine sodium. It consists of microbubble-encapsulated spheres with diameters of 2-3 µm. The clinician adds 3 million microbubbles/ml monomer (equal to a 100-fold diluted solution of perfluorobutane), as practiced in Gi, Abstract A3274, Oct. 14, 2013, Contrast-Enhanced Ultrasound with Perflubutane Microbubbles for Femoral Nerve Block—A Human Cadaver Study.

In one embodiment, the microbubbles of the present invention are phospholiquid based, such as those in Sonovue™.

According to Schneider, *Echocardiography.* 1999 October; 16(7, Pt 2):743-746, Sonovue is an echocontrast agent made of microbubbles stabilized by phospholipids and containing sulphur hexafluoride. The bubble concentration of SonoVue™ is between 100 and 500 million per ml. The mean bubble diameter is 2.5 µm and more than 90% of the bubbles are smaller than 8 µm.

It is believed that the phospholipid nature of the Sonovue microbubbles allows them to resist dissolution in nonpolar liquids, such as methylmethacrylate monomer. In particular, it is believed that the amphiphilic nature of the Sonovue microbubbles allows them to resist dissolution in nonpolar liquids.

Sonovue: On reconstitution as directed, 1 ml of the resulting dispersion contains 8 µl sulphur hexafluoride in the microbubbles, equivalent to 45 microgrammes.

In some embodiments, the plurality of microbubbles have a median $D_{50}$ particle size of between 1 um and 10 um.

In some embodiments, at least 75% of the microbubbles in the cement embodiment are smaller than 10 um; preferably at least 85%.

It is further believed that adding microbubbles to the saline-filled balloon will allow the surgeon to visualize the expanded balloon via ultrasound, and thereby allow the surgeon to visualize placement of the expanded balloon without the need for xrays.

Therefore, in accordance with the present invention, there is provided a system comprising:
a) an inflated balloon having an opening;
b) a tube connected to the opening;
c) a fluid disposed within the inflated balloon; and
d) a plurality of microbubbles dispersed within the fluid.

Preferably, the plurality of microbubbles is present in a concentration of between 1 to 10 million microbubbles/ml of the fluid.

It is further believed that, if the skilled artisan uses a dual lumen catheter common to kyphoplasty, providing microbubbles within a fluid in the inner catheter of the dual lumen also allows the clinician to monitor the placement of the inner catheter (and thereby the uninflated balloon) prior to balloon expansion.

Therefore, in accordance with the present invention, there is provided a tool comprising an outer tube 1 having a distal end 3, an inner tube 5 extending within the outer tube and having a distal end region 7 that extends beyond the distal end of the outer tube, and an expandable structure 9 having a proximal end 11 secured to the distal end of the outer tube and a distal end 13 secured to the distal end region of the inner tube, whereby the distal end region of the inner tube is enclosed within the expandable structure, wherein a first plurality of microbubbles 15 are disposed within a first fluid in the inner tube and a second plurality of microbubbles 17 are disposed within a second fluid within the expandable structure.

Preferably, the expandable structure is a balloon.

Preferably, the first fluid is saline. Preferably, the second fluid is saline.

In accordance with the present invention, there is provided a method for treating bone comprising the steps of:
  a) providing a tool comprising an outer tube having a distal end, an inner tube extending within the outer catheter tube and having a distal end region that extends beyond the distal end of the outer tube, and an expandable structure having a proximal end secured to the distal end of the outer tube and a distal end secured to the distal end region of the inner tube, whereby the distal end region of the inner tube is enclosed within the expandable structure, wherein a first plurality of microbubbles are disposed with the inner tube within a first fluid, and a second plurality of microbubbles are disposed within the expandable structure within a second fluid,
  b) manipulating the tool to introduce the expandable structure into bone while in a generally collapsed geometry,
  c) applying ultrasound to assess a location of the inner catheter,
  d) causing the expandable structure to assume an expanded geometry inside bone, and
  e) applying ultrasound to assess a location of the expandable structure.

Preferably, the microbubble concentration in the balloon or tube is in the range of 0.001 to 100 million microbubbles/ml of the fluid, preferably, in the range of 0.1 to 10 million microbubbles/ml of the fluid most preferably, in the range of 1 to 10 million microbubbles/ml of the fluid.

In some embodiments, the plurality of microbubbles in the balloon or tube have a median $D_{50}$ particle size of between 1 um and 10 um.

In some embodiments, at least 75% of the microbubbles in the balloon or tube embodiment are smaller than 10 um; preferably at least 85%.

In some embodiments, contrast specific software generally used with commercial contrast agents is used. In some Sonovue embodiments, HDI-Lab software (as disclosed in Kratzer, *Scand J Gastroenterol.* 2005 August; 40(8):985-91) is used).

In some embodiments, ultrasound is applied with a Esaote Megas GPX (Esaote, Genoa, Italy) or with a Philips HD11 XE (Philips Ultrasound, Andover, Mass., USA) ultrasononographic unit with convex, 2.5-5 MHz probes. In some Sonovue embodiments, a Philips HDI 5000 scanner. (as disclosed in Kratzer, *Scand J Gastroenterol.* 2005 August; 40(8):985-91) is used.

In one prophetic method of using the present invention, the components are mixed until the polymer is wetted by the monomer. Optionally, when wetting is 95 to 100% complete, the mixture has achieved a desired high viscosity, for example 500 Pascal-second or more. Optionally, mixing is complete within 1, 5, 10, 15, 30, 60, 90, 120 or 180 seconds. In a modern medical facility, it can be advantageous to shorten the mixing time in order to reduce the demand on physical facilities and/or medical personnel. A savings of even 1 to 2 minutes with respect to previously available alternatives can be significant. In an exemplary embodiment of the invention, mixing is conducted in a mixing apparatus of the type described in U.S. application Ser. No. 11/428, 908, the disclosure of which is fully incorporate herein by reference. After mixing is complete, a working window during which the cement remains viscous but has not fully hardened occurs. During this working window, the polymerization inhibitor contained in the acrylic powder is released, thereby impeding the polymerization reaction and thereby lengthening the working window. The duration of the working window may vary with the exact cement formulation and/or ambient conditions (e.g. temperature and/or humidity). Formulation considerations include, but are not limited to polymer MW (average and/or distribution), polymer bead size, concentrations of non-polymerizing ingredient and polymer:monomer ratio.

In a prophetic embodiment of the invention, a cement characterized by an immediate transition to high viscosity is injected during a working window in a vertebroplasty or kyphoplasty procedure. FIG. 3 is a graph of the viscosity profiles of the conventional Beyar cement and that of the present invention. It is believed that the viscosity profile of the present invention will have a rapid initial increase in viscosity (due to the wetting of a first PMMA fraction); a long working time characterized by essentially no increase in viscosity (due to the subsequent release of the reaction-stemming anti-oxidant until it is consumed), and then a later viscosity-increasing window (due to the subsequent wetting of the second PMMA fraction).

In a prophetic embodiment of the invention, cement with a viscosity profile as described above is useful in vertebral repair, for example in vertebroplasty and/or kyphoplasty procedures. It is believed that the lengthened working window of the present invention will permit a medical practitioner sufficient time to load a high pressure injection device and inject the cement into a desired location. Optionally, an injection needle or cannula is inserted into the body prior to, or concurrent with the mixing so that the window need only be long enough for loading and injection. Exemplary injection systems include the CONFIDENCE injection system marketed by DePuy Synthes Spine of Raynham, Mass.

Optionally, cement injection into a vertebra is under sufficient pressure to move fractured bone, such as vertebral plates of a collapsed vertebra. Optionally, injection of viscous cement under high pressure contributes to fracture reduction and/or restoration of vertebral height.

In a prophetic embodiment of the invention, the material (e.g., bone cement) includes processed bone (from human or animals origin) and/or synthetic bone. Optionally, the cement has osteoconductive and/or osteoinductive behavior.

In a prophetic embodiment of the invention, hardening to a hardened condition occurs after the lengthened working window. The cement hardens even if it has not been injected.

Optionally, use of cement which is viscous at the time of injection reduces the risk of material leakage and/or infiltrates into the intravertebral cancellous bone (interdigitaion)

and/or reduces the fracture. Reduced leakage optionally contributes to increased likelihood of a positive clinical outcome.

In a prophetic embodiment of the invention, cement is sufficiently viscous to move surrounding tissue as it is injected. Optionally, moving of the surrounding tissue contributes to fracture reduction and/or restoration of vertebral height.

An injected volume of cement may vary, depending upon the type and/or number of orthopedic procedures being performed. The volume injected may be, for example, 2-5 cc for a typical vertebral repair and as high as 8-12 cc or higher for repairs of other types of bones. Other volumes may be appropriate, depending for example, on the volume of space and the desired effect of the injection. In some cases, a large volume of viscous cement is loaded into a delivery device and several vertebrae are repaired in a single medical procedure. Optionally, one or more cannulae or needles are employed to perform multiple procedures.

Viscous cements according to exemplary embodiments of the invention may be delivered at a desired flow rate through standard orthopedic cannulae by applying sufficient pressure. Exemplary average injection rates may be in the range of 0.01 to 0.5 ml/sec, optionally about 0.05, about 0.075 or 0.1 ml/sec or lesser or intermediate or greater average flow rates. Optionally, the flow rate varies significantly during an injection period (e.g., pulse injections). Optionally, the flow rate is controlled manually or using electronic or mechanical circuitry. In an exemplary embodiment of the invention, medical personnel view the cement as it is being injected (e.g. via fluoroscopy) and adjust a flow rate and/or delivery volume based upon observed results. Optionally, the flow rate is adjusted and/or controlled to allow a medical practitioner to evaluate progress of the procedure based upon medical images (e.g. fluoroscopy) acquired during the procedure. In an exemplary embodiment of the invention, the cement is sufficiently viscous that advances into the body when pressure is applied above a threshold and ceases to advance when pressure is reduced below a threshold. Optionally, the threshold varies with one or more of cement viscosity, cannula diameter and cannula length.

It is contemplated that there may be poor mixing of the PI released from the PMMA particle with the liquid phase. If this becomes a concern, then the delivery cannula of the injection device can be vibrated to help achieve better mixing.

I claim:

1. A bone cement formulation comprising:
 a) a powder component comprising: i) an acrylic polymer powder, and ii) an initiator powder present in an amount defining a powder initiator fraction,
 b) a liquid component comprising i) an acrylic monomer and ii) an accelerator present in an amount defining a liquid accelerator fraction,
 c) a solution comprising a plurality of microbubbles.

2. The formulation of claim 1 wherein the plurality of microbubbles have a median $D_{50}$ particle size of between 1 um and 10 um.

3. The formulation of claim 2 wherein the acrylic polymer powder comprises PMMA.

4. The formulation of claim 1 wherein the acrylic polymer powder comprises at least 50 wt % of the powder component.

5. The formulation of claim 1 wherein the powder component further comprises iii) between 5 wt % and 35 wt % contrast agent powder.

6. The formulation of claim 1 wherein the powder component further comprises iii) between 25 wt % and 35 wt % contrast agent powder.

\* \* \* \* \*